United States Patent [19]

Record et al.

[11] Patent Number: 4,952,407

[45] Date of Patent: Aug. 28, 1990

[54] CHEWING GUM CONTAINING GLYCEROL MONO LAURATE

[75] Inventors: David W. Record, River Forest; Mansukh M. Patel, Downers Grove, both of Ill.

[73] Assignee: Wm. Wrigley Jr. Company, Chicago, Ill.

[21] Appl. No.: 243,404

[22] Filed: Sep. 12, 1988

[51] Int. Cl.$^5$ ............................................. A61K 47/20
[52] U.S. Cl. ........................................ 424/440; 426/3; 426/5
[58] Field of Search ........................ 424/440; 426/3, 5

[56] References Cited

U.S. PATENT DOCUMENTS

| | | |
|---|---|---|
| 3,857,965 | 12/1974 | Ream . |
| 4,002,775 | 1/1977 | Kabara . |
| 4,067,997 | 1/1978 | Kabara . |
| 4,088,788 | 5/1978 | Ream et al. . |
| 4,122,164 | 10/1978 | Mitchell et al. . |
| 4,151,270 | 4/1979 | Ream et al. . |
| 4,170,636 | 10/1979 | Engel et al. . |
| 4,208,432 | 6/1980 | Noborio et al. . |
| 4,252,830 | 2/1981 | Kehoe et al. ............... 426/5 |
| 4,259,358 | 3/1981 | Duthie . |
| 4,299,852 | 10/1981 | Ueno et al. . |
| 4,317,837 | 3/1982 | Kehoe et al. ............... 426/3 |
| 4,357,354 | 11/1982 | Kehoe et al. ............... 426/3 |
| 4,374,122 | 2/1983 | Stroz et al. . |
| 4,400,372 | 8/1983 | Muhler et al. . |
| 4,428,928 | 1/1984 | Muhler et al. . |
| 4,457,921 | 7/1984 | Stroz et al. . |
| 4,485,029 | 11/1984 | Kato et al. . |
| 4,500,547 | 2/1985 | Puglia et al. . |
| 4,508,713 | 4/1985 | Stroz et al. . |
| 4,557,935 | 12/1985 | Ekenstam et al. . |
| 4,568,537 | 2/1986 | Hoerman et al. . |
| 4,608,263 | 8/1986 | Bergin et al. . |
| 4,671,961 | 6/1987 | Patel et al. . |
| 4,671,967 | 6/1987 | Patel et al. . |
| 4,728,515 | 3/1988 | Patel et al. . |
| 4,828,820 | 5/1989 | Glass et al. . |

OTHER PUBLICATIONS

Symposium on the Pharmacological Effect of Lipids by J. J. Kabara.

Primary Examiner—Ellis P. Robinson
Assistant Examiner—P. L. Prater
Attorney, Agent, or Firm—Willian Brinks Olds Hofer Gilson & Lione

[57] ABSTRACT

A gum composition useful in dental plaque removal and suppression and method of use is disclosed. The composition comprises 15 to 90% gum base, 5 to 80% sweetening and bulking agents, 1 to 10% glycerine, optional color and flavor, and contains 0.25 to 0.75% glycerol mono laurate. Preferably, the composition also includes a high filler content. The method involves chewing the gum composition the invention for at least 20 minutes, preferably at least five times a day for four successive days.

20 Claims, No Drawings

CHEWING GUM CONTAINING GLYCEROL MONO LAURATE

BACKGROUND OF THE INVENTION

The present invention relates to chewing gum compositions which help to prevent formation of and remove dental plaque. More particularly, the invention relates to gum compositions containing glycerol mono laurate, and methods of use of such compositions.

The role of dental plaque in the formation of caries is well known. Also, more recently the role of plaque in periodontal disease, resulting in tooth loss in older individuals, has been commented upon.

Attempts to reduce dental plaque through the use of chewing gum, and special compositions and ingredients for use in such gums, are also known. For example, U.S. Pat. No. 4,400,372 describes a chewing gum designed to clean and polish teeth, containing non-toxic acid and calcined kaolin particles. U.S. Pat. No. 4,568,537 describes a gum formulation which, when chewed, alters the oral environment to decrease tooth demineralization, and notes that chewing gum achieves same mechanical dental cleaning.

Chewing gum compositions may also contain ingredients which, either alone or in combination with other ingredients, have a anti-cariogenic effect because of the interaction of the ingredient and *Steptococcus mutans*, the primary microorganism in the mouth which forms acid by fermenting carbohydrates, the acid causing dental caries. For example, U.S. Pat. Nos. 4,374,122 and 4,457,911 disclose that 3, 4-dihydro-6-methyl-1, 2, 3, -oxathiazine-4-one-2, 2-dioxide and hydrogenated starch hydrolysates, inhibit the growth of *Steptococcus mutans*.

Glycerol mono laurate has been identified as a food ingredient with anti-cariogenic activity. For example, an article in a symposium on the Pharmacological Effect of Lipids, The American Oil Chemists' Society (1978), describes experiments conducted by Kabara et al. with lauricidin brand glycerol mono laurate, both in vitro, and as a component of feed for rats in an in vivo test. U.S. Pat. No. 4,067,997 to Kabara describes similar tests and various compositions containing glycerol mono laurate, including a surgical scrub and a mouthwash.

SUMMARY OF THE INVENTION

Applicants have discovered that chewing gum compositions containing glycerol mono laurate have a dental plaque reducing affect, particularly where the gum also has a high filler content. The gum composition of the present invention comprises 15 to 90% gum base, 5 to 80% bulking and sweetening agents. 1 to 10% glycerine and optional color and flavor, and contains 0.1 to 1.0% glycerol mono laurate. The preferred level of glycerol mono laurate is between about 0.25 and 0.75%. Preferably, the gum composition also has a filler content at least 10% and also a high base content.

The invention also relates to a method of preventing buildup of dental plaque on teeth by chewing the gum composition of the invention for at least 20 minutes.

DETAILED DESCRIPTION OF THE PREFERRED EMBODIMENT

The gum composition of the present invention may be either chewing gum or bubble gum, both referred to herein as chewing gum. It is preferred that the gum base used be of a tack variety, to assist in the mechanical plaque removal.

The gum composition of the present invention contains many ingredients found in conventional gum compositions, and at conventional levels. Gum base usually comprises 15 to 35% of the gum. It has been found, however, that a higher gum base content adds to the gum's cud size, and promotes plaque removal. Acceptable gum bases for use in the present invention include Paloja, Astro and Magna (bubble gum base), available from L. A. Dreyfus Co., Plainfield, N.J.

Fillers are common in gum compositions, and are often included with the polymer material in making up the gum base. For purpose of the present invention, any filler in the gum base and the filler added to make the final gum composition are added together in describing the filler content of the gum composition. It is preferred that the filler content be at least 10%. and more preferably between 15 and 50%. Preferred fillers include calcium carbonate, talc, sodium bicarbonate, dicalcium phosphate and mixtures thereof. The most preferred filler is calcium carbonate, at a level of about 22–24%.

The particle size of the filler should be between 0.1 microns and 25 microns. The preferred particle size for a calcium carbonate filler is between about 0.5–10 microns, with a mean particle size of 2.5 microns.

The filler may be mixed with the base during base formulation, later during gum formulation, or a part added at each stage. It is preferred to mix the entire filler content into the base composition to alleviate the need for an extra ingredient at the gum mixing site.

Gum compositions of the present invention may include other ingredients normally found in gum, including sweeteners, flavors, color, plasticizers, processing aides and the like. Because the gum is used in promoting dental health, it is preferred to use non-cariogenic sweeteners. A preferred sweetener is xylitol.

The level of glycerol mono laurate in the gum should be between about 0.1 and about 1.0%. Preferably, the level will be about 0.25 to about 0.75%. Most preferred are compositions with about 0.5% glycerol mono laurate.

The preferred gum composition of the present invention is as follows:
37.4% base
23.8% filler
15% xylitol
12.4% sorbitol
0.5% glycerol mono laurate
2.5% flavor
6% glycerine
0.3% aspartame
0.1% color The glycerol mono laurate is believed to have several anti-plaque benefits in the gum composition of the present invention, as a surfactant, an anti-microbial agent and an anti-adherrant compound.

The method of preventing plaque buildup or removing plaque requires chewing the gum of the present invention containing glycerol mono laurate for at least 20 minutes, and preferably at least 30 minutes. Even one chewing has been found to produce detectable plaque reduction, but the preferred method of the invention involves repeated chewing of the gum, preferably five portions throughout the day for at least 20 minutes each, repeated for four successive days.

The gum composition of the present invention has been found to provide significant plaque removal, and hence the suppression of plaque buildup, when used in accordance of the method of the present invention.

It should be understood that the preferred embodiment described in detail herein is illustrative of various aspects of the invention, and that various modifications and changes to the presently preferred embodiment may be made. Therefore, the following claims, including all equivalents, define the scope of the invention.

We claim:

1. In a chewing gum composition comprising 15 to 90% gum base, 5 to 80% bulking and sweetening agents, 1 to 10% glycerine and optional color and flavor, the improvement comprising including an amount of glycerol mono laurate in the gum composition effective to reduce dental plaque.

2. The improved gum composition of claim 1 wherein the composition further includes 10 to 50% of an inorganic filler selected from the group consisting of calcium carbonate, talc, sodium bicarbonate, dicalcium phosphate and mixtures thereof.

3. The improved gum composition of claim 1 wherein the composition further comprises about 15% calcium carbonate.

4. The improved gum composition of claim 1 wherein the glycerol mono laurate comprises about 0.25 to 0.75% of the composition.

5. The improved gum composition of claim 1 wherein the glycerol mono laurate comprises about 0.25% of the composition.

6. The improved gum composition of claim 1 wherein the composition comprises about:
   (a) 38% gum base;
   (b) 15% xylitol:
   (c) 6% glycerine;
   (d) 24% calcium carbonate;
   (e) 12% sorbitol;
   (f) 2.5% flavor:
   (g) 0.1% color:
   (h) 0.3% aspartame: and
   (i) 0.5% glycerol mono laurate.

7. A method of suppressing dental plaque formation comprising the steps of:
   (a) providing a gum composition comprising about 15 to 90% gum base, about 5 to 80% of a bulking and sweetening agent, about 1 to 10% glycerine, optional flavors and coloring agents and about 0.25 to 0.75% glycerol mono laurate; and
   (b) chewing the gum composition for at least 20 minutes.

8. The method of claim 7 wherein the chewing gum is chewed for at least 30 minutes.

9. The method of claim 7 wherein the gum base in the gum composition includes a filler content of over 10%.

10. The method of claim 9 wherein the filler content is about 22-24%.

11. The method of claim 7 wherein the bulking and sweetening agent is selected from the group consisting of sorbitol, xylitol, sugar, corn syrup and mixtures thereof.

12. The method of claim 7 wherein the gum composition comprises about 10 to 50% of an inorganic filler selected from the group consisting of calcium carbonate, talc, sodium bicarbonate, dicalcium phosphate and mixtures thereof.

13. The method of claim 12 wherein the gum composition comprises about 22-24% calcium carbonate.

14. The method of claim 13 wherein the calcium carbonate has a particle size of between 0.1 and 25 microns.

15. A method of improving dental health comprising the steps of:
   (a) providing a gum composition comprising about 15 to 90% gum base, about 5 to 80% of a bulking and sweetening agent, about 1 to 10% glycerine, optional flavors and coloring agents and about 0.25 to 0.75% glycerol mono laurate: and
   (b) repeatedly chewing portions of said gum composition, so that at least five portions of said gum composition are chewed for at least 20 minutes each throughout the day for at least 4 successive days.

16. The method of claim 15 wherein the gum composition comprises a gum base having a filler content of at least 10%.

17. The method of claim 15 wherein the gum composition further includes about 15 to 50% of an inorganic filler selected from the group consisting of calcium carbonate, talc, sodium bicarbonate, dicalcium phosphate and mixture thereof.

18. The method of claim 17 wherein the inorganic filler comprises about 22-24% calcium carbonate.

19. The method of claim 15 wherein the gum composition comprises about 0.5% glycerol mono laurate.

20. The improved gum composition of claim 1 wherein the glycerol mono laurate comprises from 0.1 to 1.0% of the composition.

* * * * *